(12) United States Patent
Beard et al.

(10) Patent No.: US 11,766,344 B2
(45) Date of Patent: Sep. 26, 2023

(54) DEPLOYMENT HANDLE FOR A MEDICAL DEVICE DEPLOYMENT SYSTEM

(71) Applicant: W. L. Gore & Associates, Inc., Newark, DE (US)

(72) Inventors: Matthew S. Beard, Phoenix, AZ (US); David A. Herrin, Seattle, WA (US); Joseph N. Kennelly Ullman, Seattle, WA (US); Martin J. Sector, Gilbert, AZ (US); Justin W. Sokel, Flagstaff, AZ (US); Jared L. Van Cleave, Kirkland, WA (US)

(73) Assignee: W. L. Gore & Associates, Inc., Newark, DE (US)

( * ) Notice: Subject to any disclaimer, the term of this patent is extended or adjusted under 35 U.S.C. 154(b) by 396 days.

(21) Appl. No.: 16/944,403

(22) Filed: Jul. 31, 2020

(65) Prior Publication Data
US 2020/0360163 A1    Nov. 19, 2020

Related U.S. Application Data

(60) Division of application No. 15/828,702, filed on Dec. 1, 2017, now Pat. No. 10,765,543, which is a
(Continued)

(51) Int. Cl.
*A61F 2/95* (2013.01)
*A61F 2/966* (2013.01)

(52) U.S. Cl.
CPC .............. *A61F 2/95* (2013.01); *A61F 2/966* (2013.01); *A61F 2/9517* (2020.05)

(58) Field of Classification Search
CPC .. A61F 2/95; A61F 2/962; A61F 2/966; A61F 2002/0072; A61F 2002/011;
(Continued)

(56) References Cited

U.S. PATENT DOCUMENTS

| 5,707,376 A | 1/1998 | Kavteladze et al. |
| 5,776,141 A | 7/1998 | Klein et al. |

(Continued)

FOREIGN PATENT DOCUMENTS

| EP | 1441668 B1 | 1/2008 |
| EP | 1915113 B1 | 3/2010 |

(Continued)

OTHER PUBLICATIONS

International Preliminary Report on Patentability received for PCT Patent Application No. PCT/US15/23140, dated Oct. 13, 2016, 7 pages.
(Continued)

*Primary Examiner* — Todd J Scherbel

(57) ABSTRACT

An introducer assembly includes a first actuating mechanism for actuating a constraining sheath between a first state releasably constraining a vascular implant and a second state allowing deployment of the vascular implant; a second actuating mechanism for actuating a blocking mechanism between a blocked state for blocking other functions of the handle and an unblocked state for allowing operation of the other functions of the handle; and an operating knob operatively coupled to both of the first and second actuating mechanisms for concurrent operation of both of the first and second actuating mechanisms in response to actuation of the operating knob.

17 Claims, 9 Drawing Sheets

Related U.S. Application Data continuation of application No. 14/670,234, filed on Mar. 26, 2015, now Pat. No. 9,833,346.

(60) Provisional application No. 61/975,165, filed on Apr. 4, 2014.

(58) Field of Classification Search
CPC ...... A61F 2002/2466; A61F 2002/2484; A61F 2002/9517; A61F 2002/954; A61F 2002/9665; A61F 5/0089; A61M 25/062; A61M 2025/0681
See application file for complete search history.

(56) References Cited

U.S. PATENT DOCUMENTS

| | | | |
|---|---|---|---|
| 5,782,909 A | 7/1998 | Quiachon et al. | |
| 5,906,619 A | 5/1999 | Olson et al. | |
| 6,143,021 A | 11/2000 | Staehle | |
| 6,203,550 B1 | 3/2001 | Olson | |
| 6,352,561 B1 | 3/2002 | Leopold et al. | |
| 6,383,211 B1 | 5/2002 | Staehle | |
| 6,527,779 B1 | 3/2003 | Rourke | |
| 6,551,350 B1 | 4/2003 | Thornton et al. | |
| 6,733,521 B2 | 5/2004 | Chobotov et al. | |
| 6,743,210 B2 | 6/2004 | Hart et al. | |
| 6,755,854 B2 | 6/2004 | Gillick et al. | |
| 6,866,669 B2 | 3/2005 | Buzzard et al. | |
| 6,884,259 B2 | 4/2005 | Tran et al. | |
| 6,911,039 B2 | 6/2005 | Shiu et al. | |
| 6,926,732 B2 | 8/2005 | Derus et al. | |
| 6,939,352 B2 | 9/2005 | Buzzard et al. | |
| 6,974,471 B2 | 12/2005 | Van et al. | |
| 7,033,368 B2 | 4/2006 | Rourke | |
| 7,052,511 B2 | 5/2006 | Weldon et al. | |
| 7,066,951 B2 | 6/2006 | Chobotov | |
| 7,081,132 B2 | 7/2006 | Cook et al. | |
| 7,122,050 B2 | 10/2006 | Randall et al. | |
| 7,147,661 B2 | 12/2006 | Chobotov et al. | |
| 7,198,636 B2 | 4/2007 | Cully et al. | |
| 7,208,003 B2 | 4/2007 | Davis et al. | |
| 7,655,034 B2 | 2/2010 | Mitchell et al. | |
| 7,837,724 B2 | 11/2010 | Keeble et al. | |
| 7,938,851 B2 | 5/2011 | Olson et al. | |
| 7,976,575 B2 | 7/2011 | Hartley | |
| 8,167,927 B2 | 5/2012 | Chobotov | |
| 8,241,346 B2 | 8/2012 | Chobotov | |
| 8,257,431 B2 | 9/2012 | Henderson et al. | |
| 8,262,671 B2 | 9/2012 | Osypka | |
| 8,328,861 B2 | 12/2012 | Martin et al. | |
| 8,361,135 B2 | 1/2013 | Dittman | |
| 8,480,725 B2 | 7/2013 | Rasmussen et al. | |
| 8,968,384 B2 | 3/2015 | Pearson et al. | |
| 9,060,895 B2 | 6/2015 | Hartley et al. | |
| 9,132,025 B2 | 9/2015 | Aristizabal et al. | |
| 9,254,204 B2 | 2/2016 | Roeder et al. | |
| 9,308,349 B2 | 4/2016 | Rezac et al. | |
| 9,498,361 B2 | 11/2016 | Roeder et al. | |
| 9,585,743 B2 | 3/2017 | Cartledge et al. | |
| 9,585,774 B2 | 3/2017 | Aristizabal et al. | |
| 9,675,485 B2 | 6/2017 | Essinger et al. | |
| 9,681,968 B2 | 6/2017 | Goetz et al. | |
| 9,700,701 B2 | 7/2017 | Benjamin et al. | |
| 9,782,284 B2 | 10/2017 | Hartley et al. | |
| 9,833,346 B2 * | 12/2017 | Beard | A61F 2/966 |
| 9,937,070 B2 | 4/2018 | Skelton et al. | |
| 10,765,543 B2 * | 9/2020 | Beard | A61F 2/95 |
| 2005/0027305 A1 | 2/2005 | Shiu et al. | |
| 2005/0080476 A1 | 4/2005 | Gunderson et al. | |
| 2010/0049293 A1 | 2/2010 | Zukowski et al. | |
| 2010/0280604 A1 | 11/2010 | Zipory et al. | |
| 2012/0046652 A1 | 2/2012 | Sokel | |
| 2013/0158655 A1 | 6/2013 | Sutton et al. | |
| 2015/0230816 A1 | 8/2015 | Strobl et al. | |
| 2017/0172724 A1 | 6/2017 | Cartledge et al. | |
| 2017/0281382 A1 | 10/2017 | Lostetter et al. | |
| 2018/0153719 A1 | 6/2018 | Beard et al. | |

FOREIGN PATENT DOCUMENTS

| | | |
|---|---|---|
| EP | 1358903 B1 | 11/2011 |
| EP | 1474074 B1 | 4/2014 |
| EP | 2749251 B1 | 7/2016 |
| EP | 2956198 B1 | 11/2017 |
| WO | 03/68302 A2 | 8/2003 |
| WO | 2012/164293 A1 | 12/2012 |

OTHER PUBLICATIONS

International Search Report and Written Opinion for PCT/US2015/023140 dated Aug. 7, 2015, corresponding to U.S. Appl. No. 14/670,234, 5 pages.

* cited by examiner

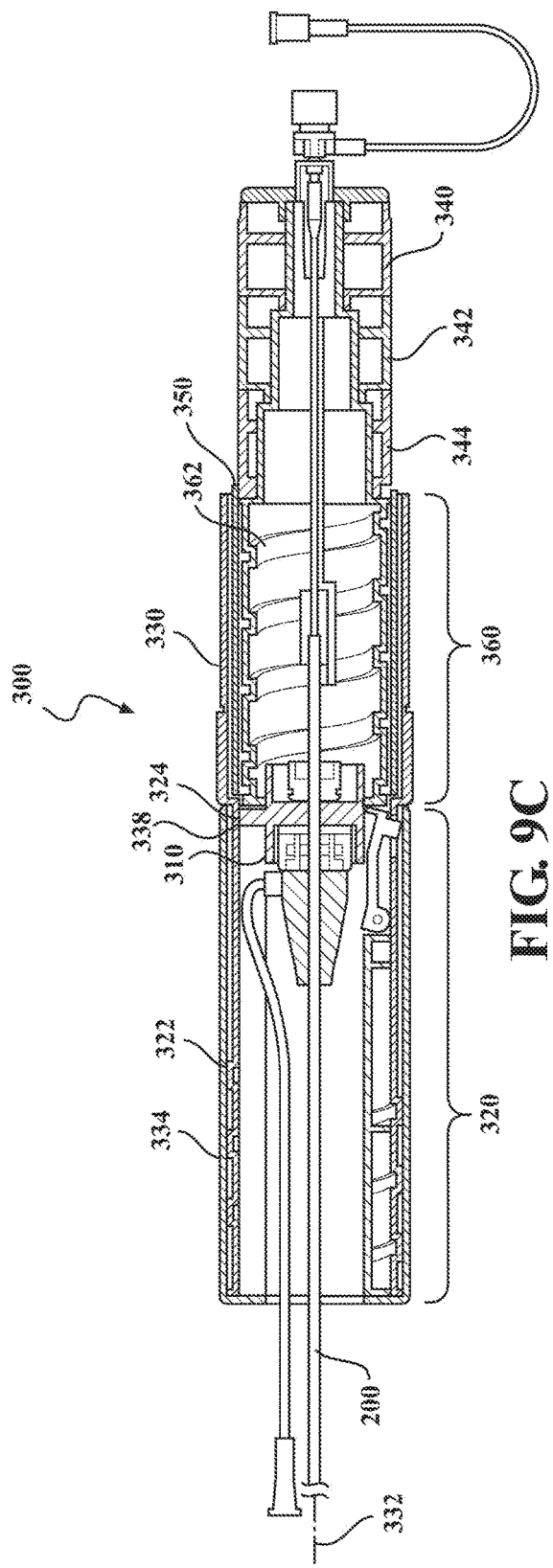
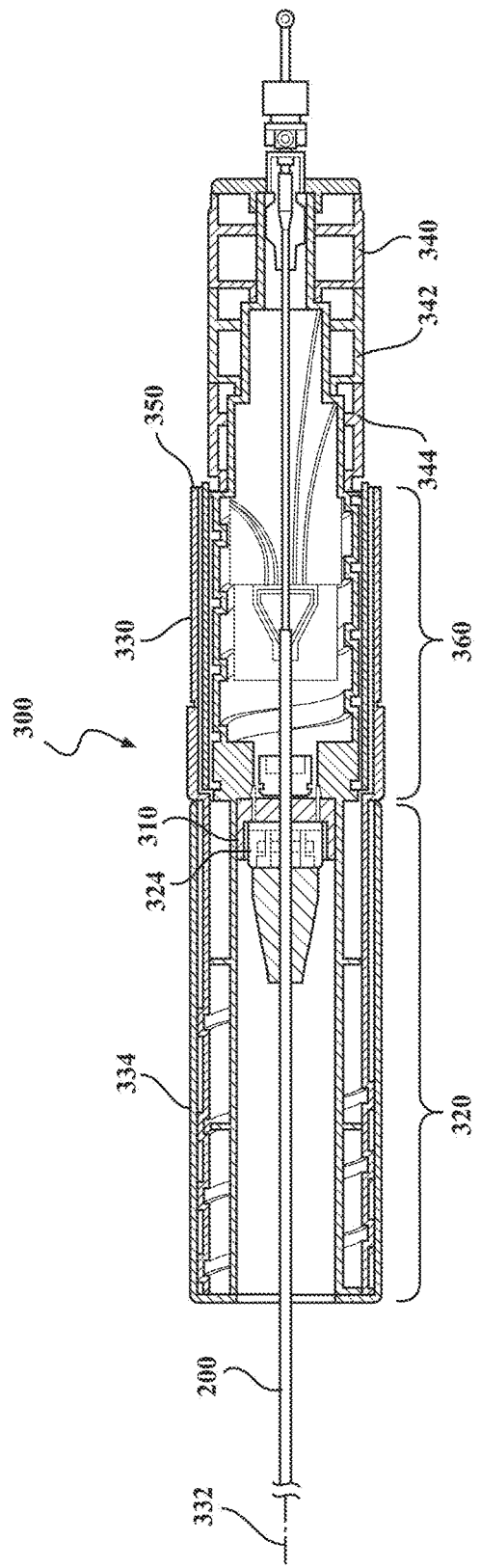
FIG. 9C
FIG. 9D

DEPLOYMENT HANDLE FOR A MEDICAL DEVICE DEPLOYMENT SYSTEM

CROSS-REFERENCE TO RELATED APPLICATION

This application is a divisional of U.S. patent application Ser. No. 15/828,702, filed Dec. 1, 2017, which is a continuation of U.S. patent application Ser. No. 14/670,234, filed Mar. 26, 2015, now U.S. Pat. No. 9,833,346, issued Dec. 5, 2017, which claims the benefit of U.S. Provisional Application 61/975,165, filed Apr. 4, 2014, all of which are incorporated herein by reference in their entireties for all purposes.

BACKGROUND

Field

The present disclosure relates to medical device deployment systems. More particularly, the present disclosure relates to a handle for a medical device deployment system.

Discussion of the Related Art

There is a need for advanced devices, tools, systems and methods used for the endoluminal treatment of aortic diseases. In particular, there remains a need for deployment systems that can accommodate increasingly complex modes of deployment of a device, such as steering, reconstraining, multiple stage deployment, multiple device deployment, while promoting ease of use to the clinician.

BRIEF DESCRIPTION OF THE DRAWINGS

The accompanying drawings are included to provide a further understanding of the present disclosure and are incorporated in and constitute a part of this specification, illustrate embodiments of the present disclosure, and together with the description serve to explain the principles of the present disclosure.

FIGS. 9C and 9D are top and front elevational views, respectively, of a handle of the introducer assembly in a second state.

DETAILED DESCRIPTION

Introducer assemblies for endoluminal delivery of vascular implants in accordance with various embodiments are disclosed for allowing actuation or deployment of a vascular implant, while forcing a particular order of operation of the handle by a clinician.

Figure 1:
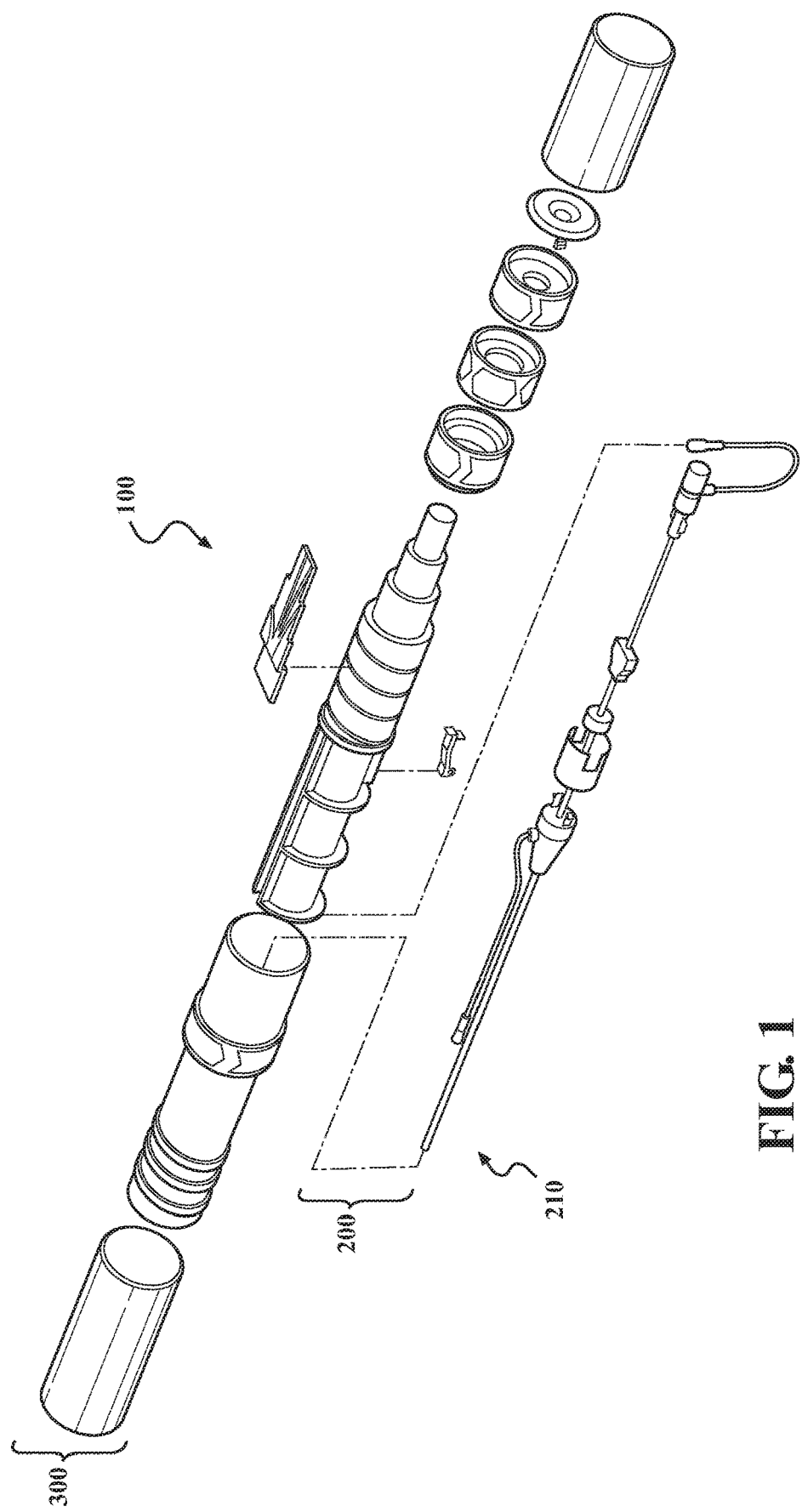
FIGS. 1 is an exploded perspective view of an introducer assembly in accordance with the present disclosure.

In various embodiments, an introducer assembly includes a first actuating mechanism for actuating a constraining sheath between a first state releasably constraining a vascular implant and a second state allowing deployment of the vascular implant; a second actuating mechanism for actuating a blocking mechanism between a blocked state for blocking one or more other knobs and/or other functions of the handle and an unblocked state for allowing operation of the one or more other knobs and/or other functions of the handle; and an operating knob operatively coupled to both of the first and second actuating mechanisms for concurrent operation of both of the first and second actuating mechanisms in response to actuation of the operating knob. An example of such an introducer assembly is generally indicated at 100 in FIG. 1. The introducer assembly 100 includes a sheath 200 and a handle 300. The introducer assembly 100 includes a constraint (not shown) for releasably constraining a vascular implant toward a distal end 210 of the sheath 200. The constraint has a first state releasably constraining an expandable implant toward a delivery configuration suitable for endoluminal delivery, and a second state released to allow expansion of the implant from the delivery configuration toward a deployed configuration. The handle includes an actuating member operatively coupled to the constraint for actuating the constraint between the first state and the second state.

In various embodiments, the constraint can include a film sleeve that extends around the implant. In the first state, opposite portions or edges of the film sleeve can be releasably held or sewn together by an elongated member, such as a wire or fiber, to maintain the implant in the delivery configuration. In such embodiments, the sleeve can be opened, or otherwise disrupted, by displacing, unstitching or otherwise disengaging the elongated member from the film sleeve to allow expansion of the implant. Further details of such constraining sleeves can be found, for example, U.S. Pat. No. 6,352,561 issued to Leopold, et al., and U.S. Pat. No. 6,551,350 issued to Thornton, et al., the content of which is incorporated herein by reference in its entirety. In such embodiments, the actuating member can be coupled to the elongated member to release or open the film sleeve from the first state to the second state.

In other embodiments, the constraint can include an axially displaceable tube, wherein such a tube can be formed from a wrapped film tube or an extruded polymer. Indeed, in various embodiments, the sheath itself could be such a constraint, wherein the sheath in the first state extends over the implant to retain the implant toward the delivery configuration. The sheath can be displaced toward the second state to allow expansion of the implant from the delivery configuration. In such embodiments, the actuating member can be coupled to the sheath so that the sheath is displaced with the actuating member between the first state and second state.

Thus, the actuating member can be configured for deploying an implant from either type of constraint described above, or other similarly actuated constraint mechanisms known in the art. The latter type of integrated sheath and constraint are described below in connection with the illustrated embodiments.

Referring to FIGS. 9A-9D, the handle 300 includes an actuating member 310 coupled to the sheath 200 for actuating the sheath 200 between the first state and second state in response to linear displacement of the actuating member 310 between a first position and a second position, respectively. The handle 300 includes a first actuating mechanism 320 for displacing the actuating member 310 between the first position and the second position.

Figure 9A:
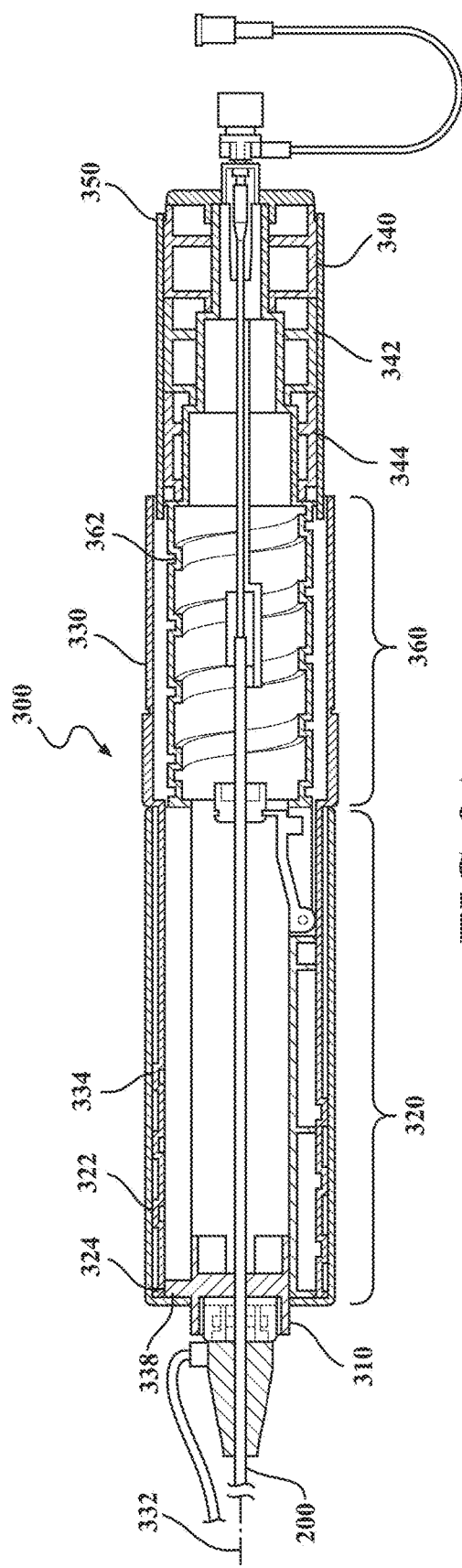
FIGS. 9A and 9B are top and front elevational views, respectively, of a handle of the introducer assembly in a first state.
Figure 9B:
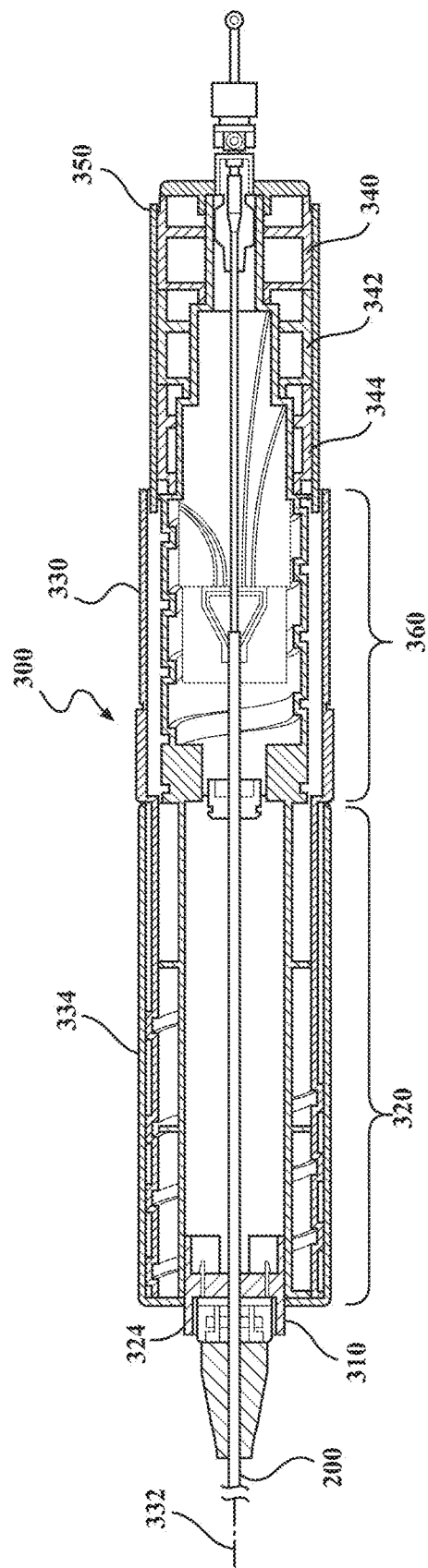

The handle 300 includes a main knob 330 for operating the first actuating mechanism 320. Described further below, the handle 300 can include one or more additional knobs to operate one or more additional separate handle functions. The handle 300 includes a cover 350 operable for movement between a covered state covering the one or more additional knobs 340, 342, 344 as shown in FIGS. 9A and 9B, and an uncovered state allowing access to the one or more additional knobs 340, 342, 344 as shown in FIGS. 9C and 9D. The handle 300 includes a second actuating mechanism 360 for displacing the cover 350 between the covered state and the uncovered state. The main knob 330 is operatively coupled to both of the first actuating mechanism 320 and the second actuating mechanism 360 to cause displacement of both the actuating member 310 between the first state and the second state and the cover 350 between the covered state and the uncovered state, respectively, in response to corresponding operation of the main knob 330.

Figure 10:
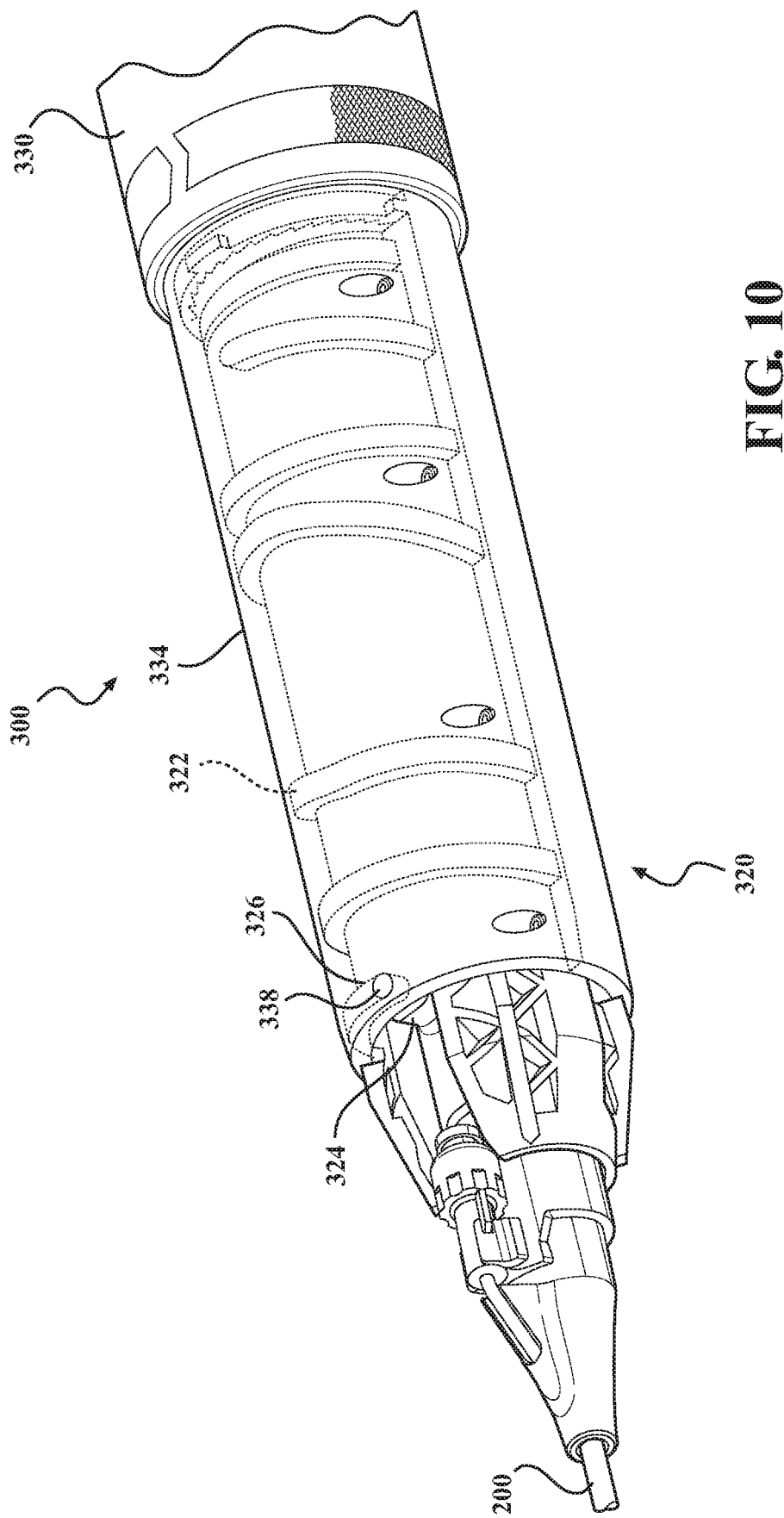
FIG. 10 is a perspective view of a front portion of the introducer assembly.
Figure 11:
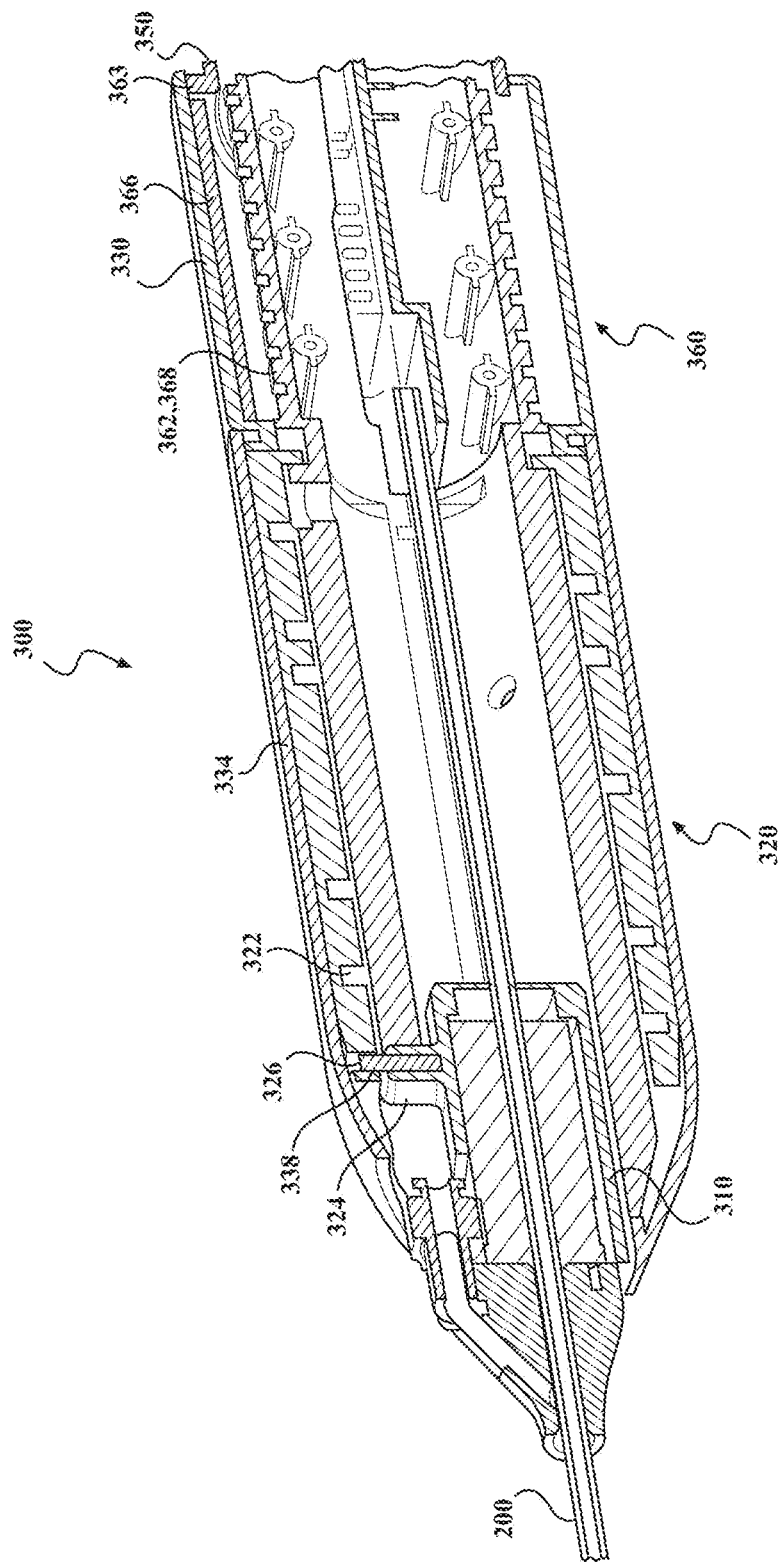
FIG. 11 is a cross-sectional view of a front portion of the introducer assembly.

In various embodiments, an actuating knob of the handle can be configured for rotation about an axis, and an actuating member for actuating one or more functions of the handle can be configured for displacement along and/or about the axis between operating states in response to corresponding rotation of the actuating knob. For example, as shown in FIGS. 9A-9D, the main knob 330 is rotatable about a rotational axis 332. The actuating member 310 is movable linearly along the axis 332 between the first state and second state. Referring to FIGS. 10 and 11, the first actuating mechanism 320 includes a first helical guide 322 movable with the main knob 330 about the axis 332. The first actuating mechanism 320 includes a first follower 324 on the actuating member 310 engaged with the first helical guide 322 to cause linear movement of the actuating member 310 between the first state and second state in response to corresponding rotation of the main knob 330. The main knob 330 includes a receiving tube 334 receiving at least a portion of the actuating member 310 therethrough as the actuating member 310 moves between the first state and second state. In a number of embodiments, for example as shown in FIGS. 10-11, the first helical guide 322 is a first helical slot 326 formed along an inner surface 336 of the receiving tube 334 and the first follower 324 includes an outwardly extending first pin 338 engaged with the helical slot 326.

Figure 12:
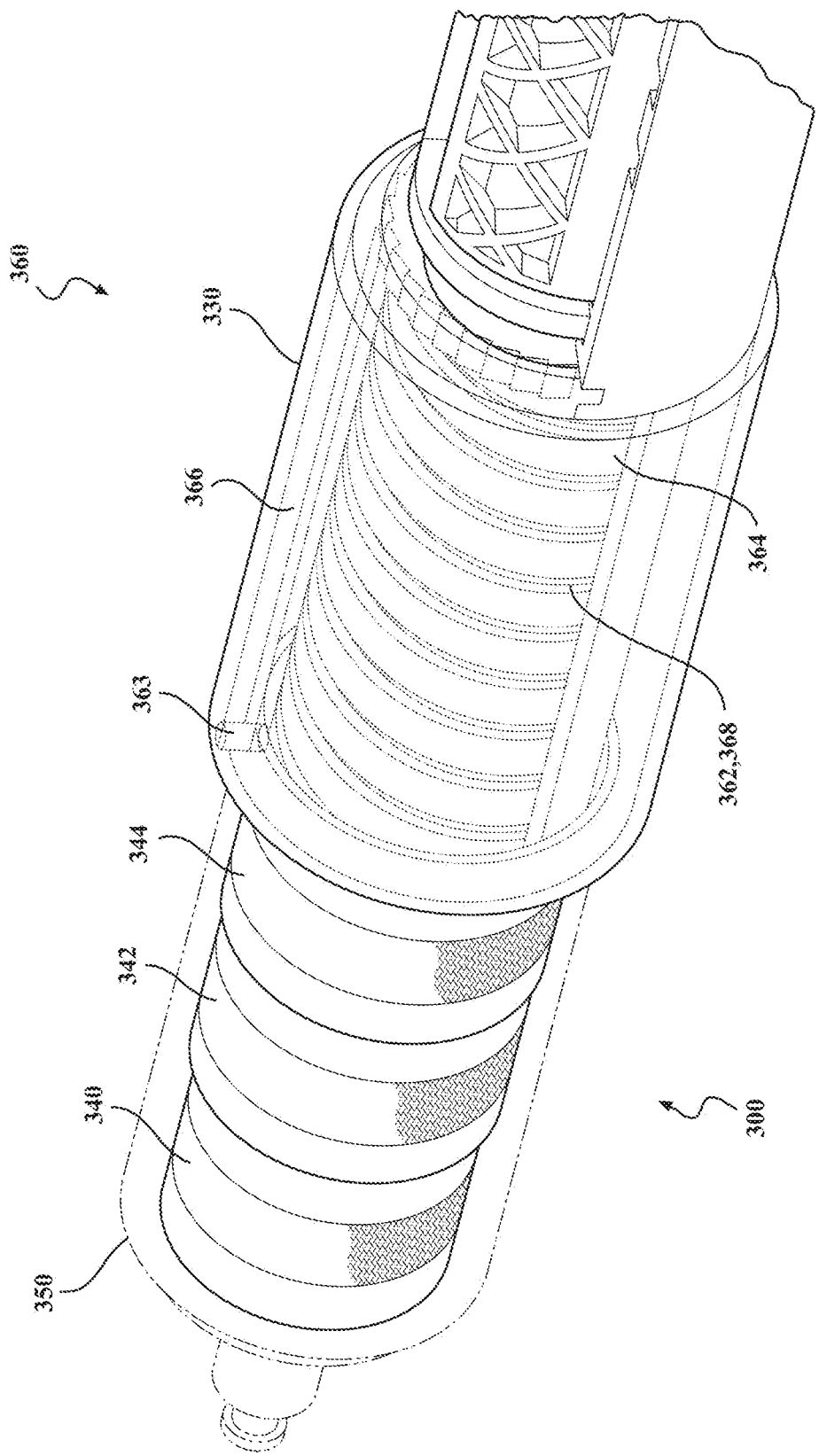
FIG. 12 is a perspective view of a rear portion of the introducer assembly.
Figure 13:
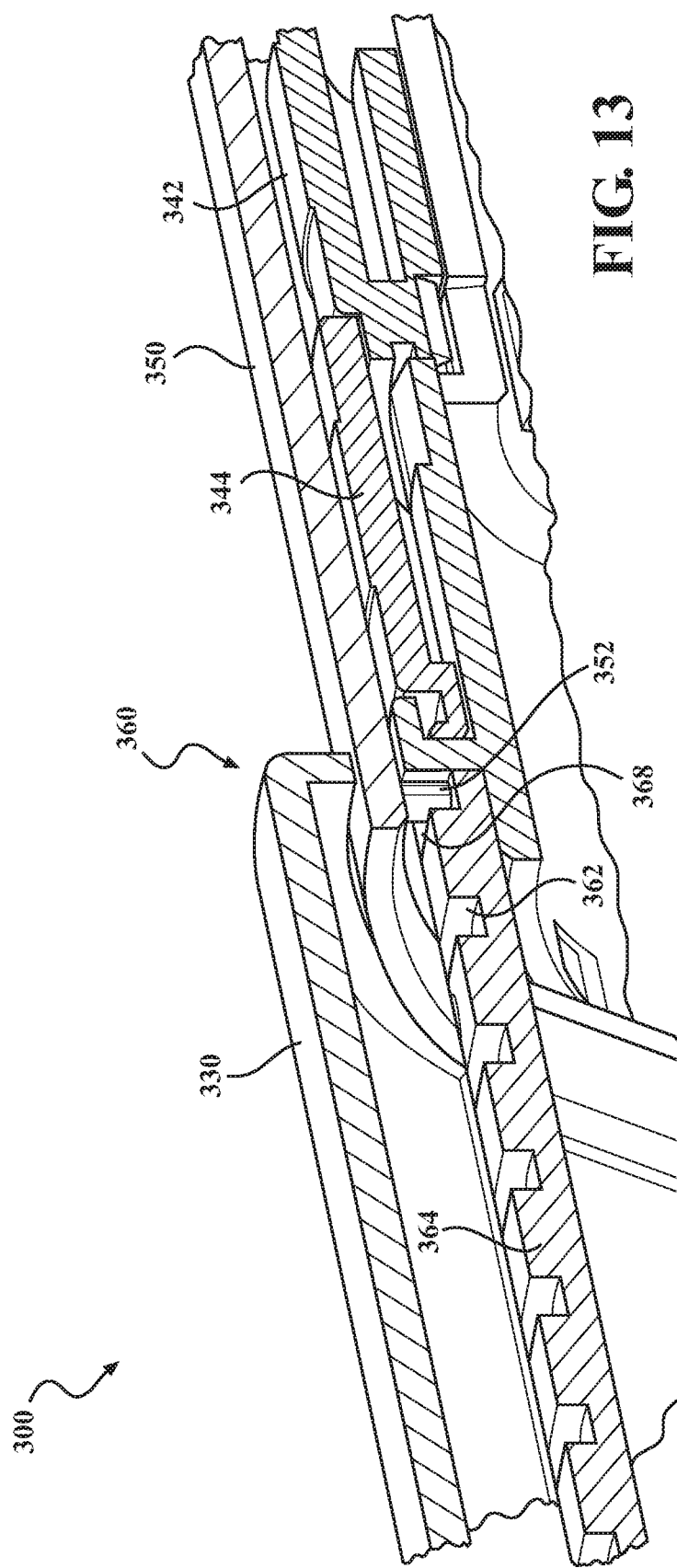
FIG. 13 is a cross sectional view of a rear portion of the introducer assembly.

Referring to FIG. 12, the second actuating mechanism 360 includes a second helical guide 362 that translates rotation of the main knob 330 to axial displacement of the cover 350. In one embodiment, the second helical guide 362 comprises a second helical slot 368 formed along an outer surface 366 of a spindle 364, the spindle 364 being aligned with the axis 332 (FIG. 9A-9D) of the main knob 330. The second actuating mechanism 360 also includes a longitudinal slot 366 formed along the main knob 330. In various embodiments, the slot 366 is parallel with the axis 332 of the main knob 330. The second actuating mechanism 360 includes a second pin 363 extending from the cover 350 and slidably engaged with the longitudinal slot 366. As best shown in FIG. 13, the second actuating mechanism 360 includes a third pin 352 extending from the cover 350 and engaging the second helical slot 368 to cause displacement of the cover 350 between the covered state and the uncovered state in response to corresponding rotation of the main knob 330.

The actuating mechanisms of the handle can be configured so that functions, such as displacements of the actuating member and cover, are delayed or accelerated relative to each other during operation of the main knob. For example, the first helical guide can include a flat or reduced or increased pitch to cause a delay, decrease or increase, respectively, in the displacement of the actuating mechanism relative to the cover in response to operation of the main knob.

In various embodiments, the handle can include a ratchet mechanism that allows actuation of an actuating knob in a first direction and prevents rotation of the actuating knob in an opposite second direction. For example, the handle can include a ratchet mechanism having a gear rack on the main knob and a fixed pawl that engages the gear rack to allow rotation of the main knob in a first direction as the pawl slips along teeth of the gear rack and that limits rotation of the main knob in an opposite second direction as the pawl catches a tooth on the gear rack. The pawl can be a spring-loaded machined component or alternatively, the pawl can be formed from spring leaf metal. The pawl can be configured to generate audible noise and/or at least provide tactile feedback as the pawl slips along the teeth of the gear rack. Optionally, one or more of the teeth of the gear rack can be sized and/or shaped differently from the other teeth of the gear rack to cause a distinct change in sound, e.g. pitch, or tactile feedback, e.g. clicks, resistance, that indicates to a clinician when a certain step in the deployment is achieved.

Figure 2:
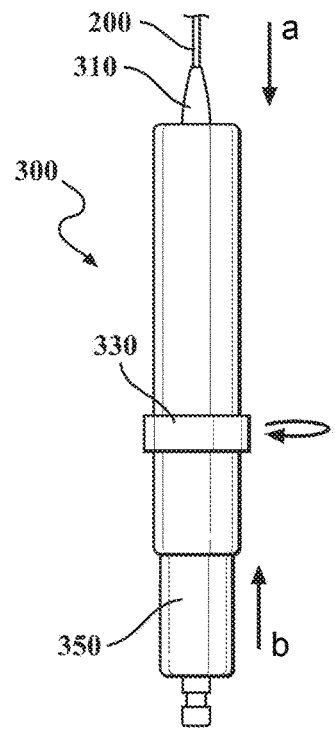
FIGS. 2-8 illustrate various states of a handle of the introducer assembly of FIG. 1.

In use, rotation of the main knob 330 about the axis 332 simultaneously operates the first actuating mechanism 320 to cause displacement of the actuating member 310 in a first direction, as indicated at arrow "a" in FIG. 2, and the second actuating mechanism 360 to cause displacement of the cover 350 in a second direction, as indicated at arrow "b" in FIG. 2. Displacement of the actuating member 310 in the first direction "a" causes corresponding displacement of the sheath 200 to allow expansion of the expandable implant 400 outwardly from the delivery configuration. The expandable vascular implant can be a self-expanding stent graft or, alternatively, a balloon-expanded implant. Displacement of the cover 350 in the second direction "b" can reveal one or more additional knobs each for operating one or more other handle functions.

Figure 3:
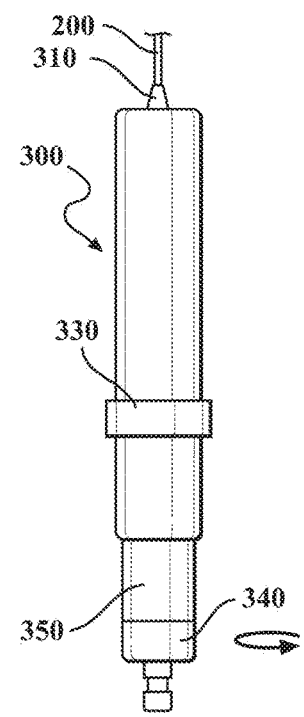

For example, as illustrated in FIG. 3, a second knob 340 is revealed after displacement of the cover 350 for operating a constraining mechanism for selectively constraining at least a portion of the implant to allow positioning of the device prior to committing to a full deployment of the implant at the treatment site. A detailed description of constraining mechanisms, construction and methods of use of such constraining mechanisms are provided in co-pending application U.S. Patent Application Publication US 2010/0049293 A1 (Zukowski et al.), the content of which is incorporated herein by reference in its entirety.

In various embodiments, the handle can be configured so that the cover can be displaced in steps to reveal additional knobs each for operating one or more other handle functions.

Figure 4:
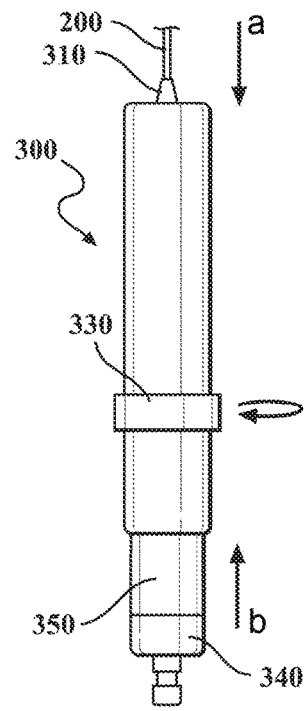
Figure 5:
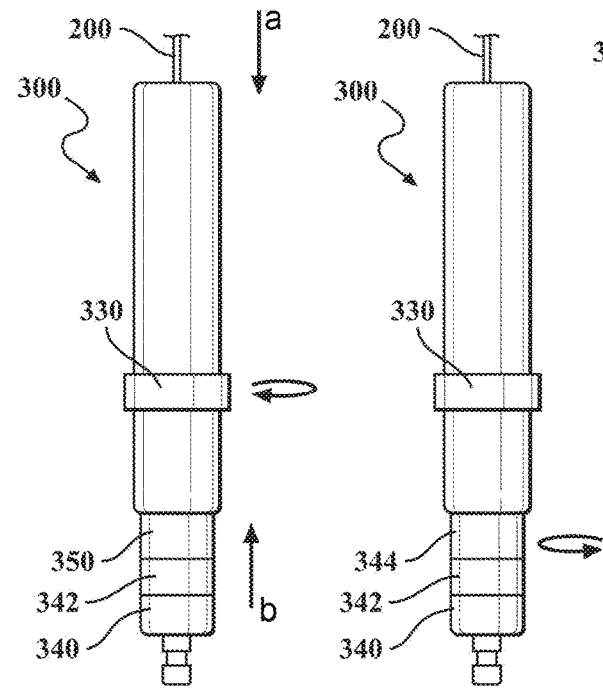

Continued rotation of the main knob 330, for example, as illustrated in FIG. 4, causes further displacement of the cover 350 in the second direction "b" to reveal a third knob 342, as shown in FIG. 5. The third knob 342 can be configured to actuate one or more other handle functions, such as displacing fibers, wires, levers, gears or any combination thereof of a steering mechanism (not shown) for selectively bending or otherwise steering at least a portion of the implant 400 during deployment.

Figures 6, 7:
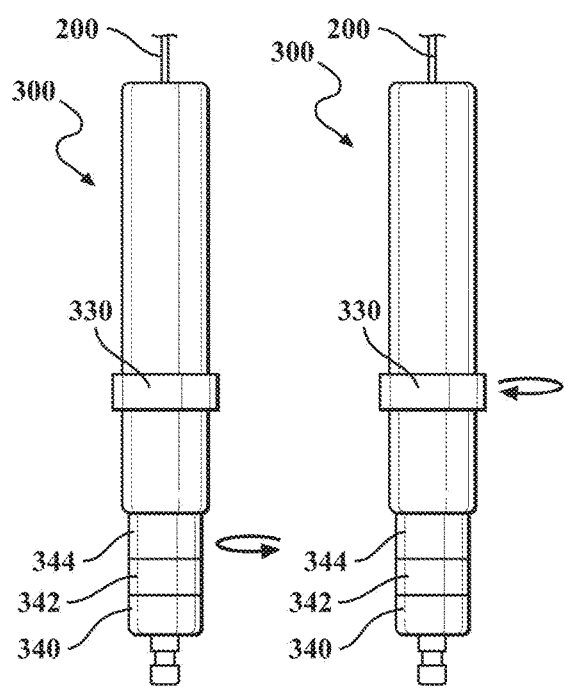
Figure 8:
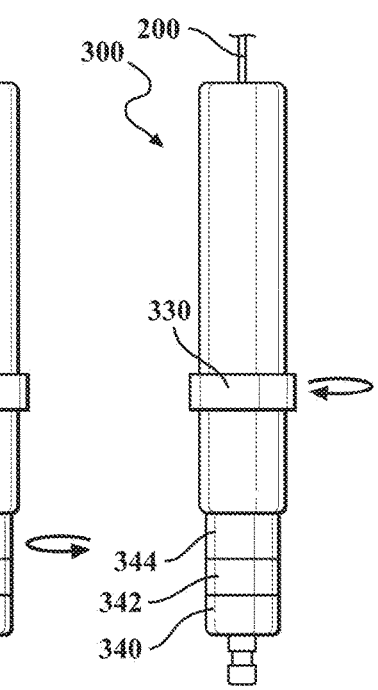

Continued rotation of the main knob 330, for example, as illustrated in FIG. 6, causes further displacement of the cover 350 in the second direction "b" to reveal a fourth knob 344, as shown in FIGS. 7-8. The fourth knob 344 can be configured to actuate one or more other handle functions, such as displacing fibers, wires, levers, gears or any combination thereof of a release mechanism. In one embodiment, a release mechanism can include a lock wire frictionally engaged with the implant to maintain a releasable coupling between the implant and the handle. The lock wire can be operatively coupled to the fourth knob to be displaced relative to and disengaged from the implant in response to actuation of the fourth knob. For example, the lock wire can be wound about a spindle portion of the fourth knob during rotation of the fourth knob. Winding of the lock wire about the spindle displaces the lock wire relative to the implant until the lock wire disengages from the implant.

In various embodiments, handle functions, such as steering, re-constraining, and deploying of an expandable implant can be operated by actuating the one or more knobs of the handle, while maintaining the implant at an intermediate configuration within a secondary or intermediate sheath or sleeve, wherein the intermediate configuration is larger than the delivery configuration and smaller than a deployed configuration. For example, the introducer assembly can include a secondary sheath for limiting expansion of the implant to an intermediate configuration after displacement of the constraining sheath. The secondary sheath can include a flexible film constraining sleeve that extends over and releasably constrains the implant. An elongated coupling member, such as a fiber or wire, stitches opposing edges or sides of the constraining sleeve together to releasably constrain the implant toward the intermediate configuration. The constraining sleeve can be opened by de-coupling the coupling member from the constraining sleeve. Further details of materials and general construction of constraining sleeves can be found in U.S. Pat. No. 6,352,561 to Leopold et al.

Figure 14:
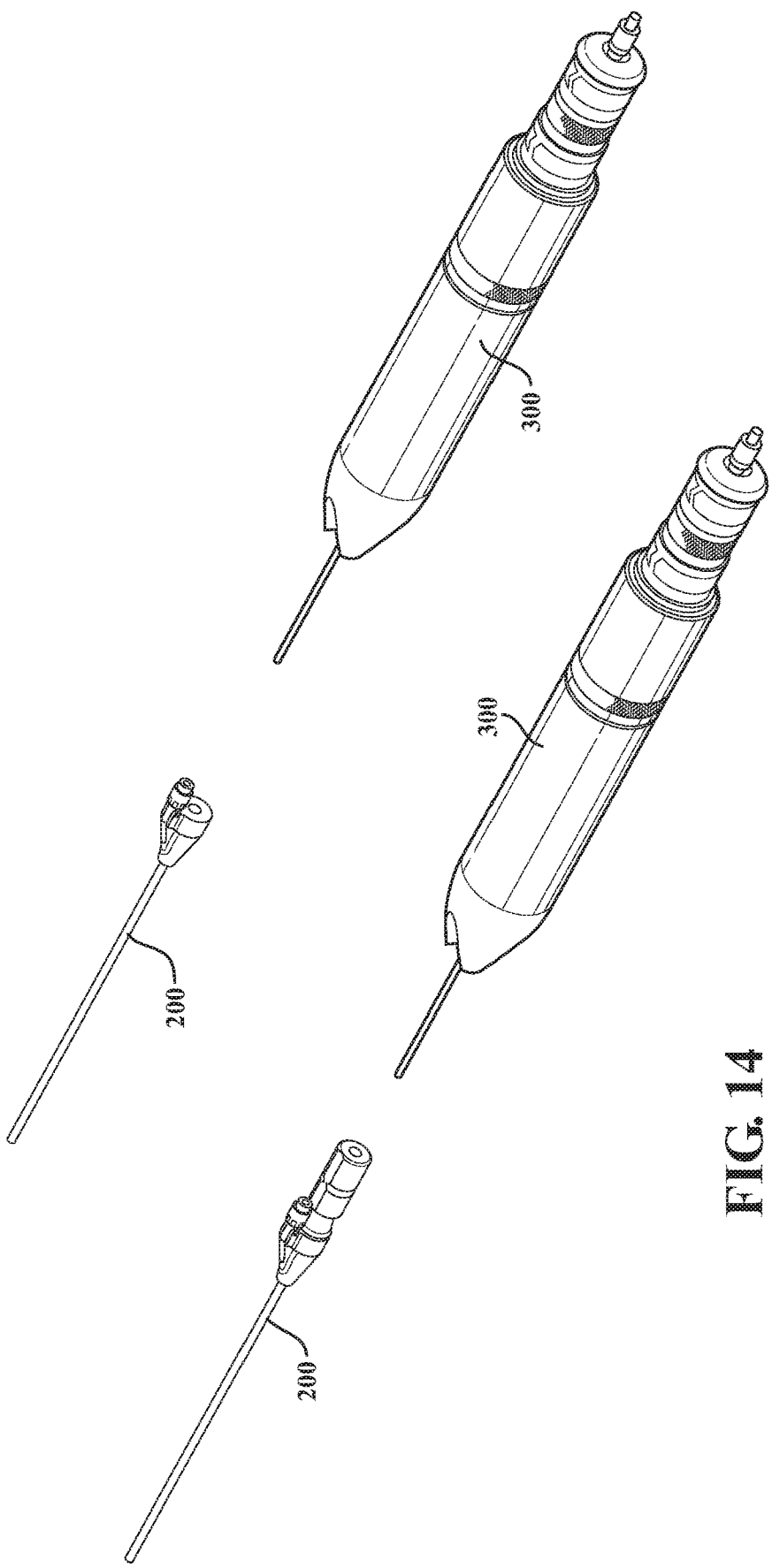
FIG. 14 illustrates perspective views of a handle and sheath of an introducer assembly decoupled from each other.

Referring to FIG. 14, the sheath 200 and handle 300 can be releasably coupled to each other for subsequent re-use of the sheath 200 as an introducer for other surgical implements after deployment of the device and de-coupling of the handle from the introducer. For example, the introducer and handle can be threaded or keyed with a slot-pin arrangement to form a releasable coupling that allows separation of the handle after deployment of the device and subsequent re-use or re-purposing of the introducer for introducing other surgical implements, such as other devices, tools, probes, cameras, drugs and saline.

It will be apparent to those skilled in the art that various modifications and variations can be made in the present disclosure without departing from the spirit or scope of the present disclosure. Thus, it is intended that the present disclosure cover the modifications and variations of this present disclosure provided they come within the scope of the appended claims and their equivalents.

What is claimed is:

1. A method of deploying a medical device comprising:
   providing a deployment handle operably coupled to the medical device, the deployment handle including a first actuation member positioned at a first longitudinal position, a second actuation member, and a cover positioned at a second longitudinal position and operably coupled to the first actuation member and disposed over the second actuation member in the second longitudinal position such that the second actuation member is inaccessible;
   advancing the medical device to a treatment region; and
   actuating the first actuation member to transition the cover from the second longitudinal position to a third longitudinal position where the second actuation member is accessible, wherein actuating the first actuation member includes rotating the first actuation member, wherein rotating the first actuation member results in lateral translation of the cover.

2. The method of claim 1, wherein actuating the first actuation member includes rotating the first actuation member about a longitudinal axis of the deployment handle.

3. The method of claim 1, further comprising actuating the second actuation member, wherein actuating the second actuation member includes rotating the second actuation member about a longitudinal axis of the deployment handle.

4. The method of claim 1, wherein actuating the first actuation member causes the cover to translate along a longitudinal axis of the deployment handle to the third longitudinal position.

5. The method of claim 1, wherein the first actuation member is operably coupled to a constraining sheath that surrounds and constrains the medical device in a delivery configuration, and wherein actuating the first actuation member causes concurrent operation of both of the cover and constraining sheath.

6. The method of claim 5, wherein the cover and the constraining sheath move in opposing directions during actuation of the first actuation member.

7. The method of claim 1, wherein the first actuation member remains at the first longitudinal position after actuating the first actuation member.

8. The method of claim 1, wherein the first actuation member is operable to rotate relative to the cover.

9. The method of claim 1, wherein the first actuation member is positioned at an outer circumference of the deployment handle.

10. A method of deploying a medical device comprising:
    advancing the medical device to a treatment region with a delivery system including a deployment handle, the deployment handle including a first actuation member positioned at a first longitudinal position, a second actuation member, and a cover positioned at a second longitudinal position and operably coupled to the first actuation member and disposed over the second actuation member in the second longitudinal position such that the second actuation member is inaccessible; and
    actuating the first actuation member such that the cover is transitioned from the second longitudinal position to a third longitudinal position, the third longitudinal position including the second actuation member being accessible, wherein actuating the first actuation member includes rotating the first actuation member about a longitudinal axis of the deployment handle.

11. The method of claim 10, further comprising actuating the second actuation member, wherein actuating the second actuation member includes rotating the second actuation member about the longitudinal axis of the deployment handle.

12. The method of claim 10, wherein actuating the first actuation member causes the cover to translate along the longitudinal axis of the deployment handle to the third longitudinal position.

13. The method of claim 10, wherein the first actuation member is operably coupled to a constraining sheath that surrounds and constrains the medical device in a delivery configuration, and wherein actuating the first actuation member causes concurrent operation of both of the cover and constraining sheath.

14. The method of claim 13, wherein the cover and the constraining sheath move in opposing directions during actuation of the first actuation member.

15. A method of deploying a medical device comprising:
advancing the medical device to a treatment region with a delivery system including a deployment handle, the deployment handle including a first actuation member at a first longitudinal position along the handle, a second actuation member, and a cover positioned at a second longitudinal position along the handle and operably coupled to the first actuation member, the cover being disposed over the second actuation member in the second longitudinal position rendering the second actuation member inaccessible; and
transitioning the cover from the second longitudinal position to a third longitudinal position where the second actuation member is rendered accessible, wherein the first actuation member is operable to rotate relative to the cover.

16. The method of claim 15, wherein actuating the first actuation member includes rotating the first actuation member, wherein rotating the first actuation member results in lateral translation of the cover.

17. The method of claim 15, wherein the first actuation member is positioned at an outer circumference of the deployment handle.

\* \* \* \* \*